United States Patent
Margner

(10) Patent No.: US 10,005,574 B2
(45) Date of Patent: Jun. 26, 2018

(54) METHOD AND DEVICE FOR HANDLING TEST TUBES IN A LABORATORY AUTOMATION SYSTEM

(71) Applicant: Roche Diagnostics Operations, Inc., Indianapolis, IN (US)

(72) Inventor: Lech Margner, Leonberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days. days.

(21) Appl. No.: 15/016,935

(22) Filed: Feb. 5, 2016

(65) Prior Publication Data
US 2016/0229565 A1    Aug. 11, 2016

(30) Foreign Application Priority Data
Feb. 11, 2015   (EP) .................................... 15154675

(51) Int. Cl.
| | |
|---|---|
| B65B 7/28 | (2006.01) |
| B65B 7/16 | (2006.01) |
| G01N 35/02 | (2006.01) |
| G01N 35/00 | (2006.01) |
| G01N 35/04 | (2006.01) |

(52) U.S. Cl.
CPC ............... *B65B 7/28* (2013.01); *B65B 7/161* (2013.01); *G01N 35/0099* (2013.01); *G01N 35/026* (2013.01); *G01N 35/04* (2013.01); *G01N 2035/0405* (2013.01)

(58) Field of Classification Search
CPC .................... B01L 3/50825; G01N 2035/0405
See application file for complete search history.

(56) References Cited

U.S. PATENT DOCUMENTS

| | | | |
|---|---|---|---|
| 2002/0009391 A1 | 1/2002 | Marquiss et al. | |
| 2005/0026295 A1* | 2/2005 | Harding | B01L 9/06 436/43 |
| 2005/0260101 A1 | 11/2005 | Nauck et al. | |
| 2007/0248496 A1* | 10/2007 | Bondioli | B65B 7/161 422/400 |

FOREIGN PATENT DOCUMENTS

EP    1524525 A1    4/2005

* cited by examiner

*Primary Examiner* — P. Kathryn Wright
(74) *Attorney, Agent, or Firm* — Roche Diagnostics Operations, Inc.

(57) ABSTRACT

A method and a device for handling test tubes in a laboratory automation system are presented. During the handling, an open end of the test tube is covered by a residue-free removable, flat cover element forced against the open end of the test tube.

6 Claims, 3 Drawing Sheets

METHOD AND DEVICE FOR HANDLING TEST TUBES IN A LABORATORY AUTOMATION SYSTEM

CROSS-REFERENCE TO RELATED APPLICATIONS

This application is a continuation of EP 15154675.1, filed Feb. 11, 2015, which is hereby incorporated by reference.

BACKGROUND

The present disclosure generally relates to a method and a device for handling test tubes in a laboratory automation system.

A laboratory automation system comprises a number of pre-analytical, analytical and/or post-analytical stations, in which samples, for example blood, saliva, swab and other specimens taken from the human body, are processed. It is generally known to provide test tubes containing the samples. The test tubes are also referred to as sample tubes. It is well known to place several test tubes in so-called racks for an efficient handling. During processing, or for sorting prior to a further processing, test tubes have to be moved or transferred, for example, from a first position within a rack to a second position within the same rack or to a different rack and/or from a first station to a second station. Prior to processing, the test tubes are usually capped with a removable plug or stopper. For processing the samples, the test tubes are decapped.

When handling an open test tube, it is known to choose the velocity and/or acceleration of the handling device sufficiently low in order to prevent the sample from sloshing out of the test tube or spilling.

Therefore, there is a need for a method and a device for an improved handling of open test tubes in a laboratory automation system.

SUMMARY

According to the present disclosure, a device and method for handling an open test tube in a laboratory automation system are presented. The method can comprise covering an open end of the test tube by a residue-free, removable, flat cover element during the handling and forcing the cover element against the open end of the test tube.

Accordingly, it is a feature of the embodiments of the present disclosure to provide a method and a device for an improved handling of open test tubes in a laboratory automation system. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
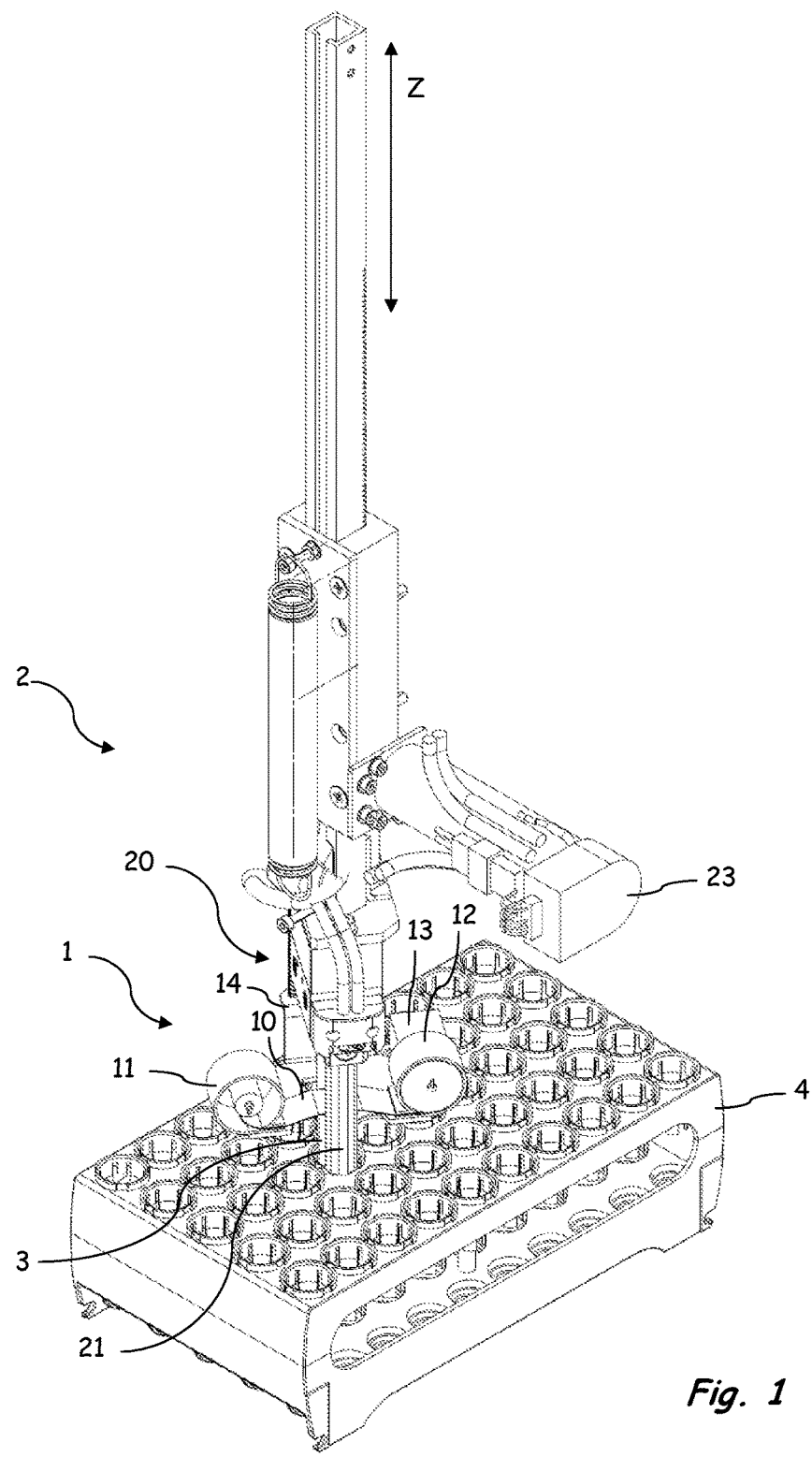
FIG. 1 illustrates a perspective view of a device for handling open test tubes according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A method for handling an open test tube in a laboratory automation system is provided. During the handling, an open end of the test tube can be covered with a residue-free, removable, flat cover element forced against the open end of the test tube.

In the context of the application, the term "cover" can be to be understood as meaning that the element can abut the open end of the test tube without combining the elements by a structural connection, adhesive or the like.

By the use of the cover element, the test tube can be temporarily covered to prevent the sample from sloshing out of the test tube or spilling while moving the test tube. Covering the test tubes can permit a handling of the test tubes at high velocities and/or high accelerations. Hence, in contrast to the prior art, it may not be necessary to lower the speed of a manipulator handling the test tubes even in case of high fill levels within the test tubes. In contrast to a closing of the open end by a plug or other closing elements fitted into the opening at the open end, the flat cover element can allow temporarily covering the open end without the necessity of an additional decapping step after releasing the test tube. The cover element can be placed against the open end of the test tube upon picking up the test tube and can be removed from test tube upon releasing the test tube. The cover element can be a flat, flexible structure, such as a sheet or a foil.

In some embodiments, the cover element can be a tape covering the open end of the test tube. The tape can be oriented with its flat surface abutting against the open end of the test tube. In some embodiments, the tape can be stretched over the open end to sealingly cling to the contour of the open end. It may be obvious to the person skilled in the art that the width of the tape can be chosen to match the size of the open end of the test tube. The width can be chosen to be larger than the width of the open end so that the tape can overlap an outer edge of the test tube.

For securely forcing the tape against the open end, in some embodiments, the tape can be held under tension by forcing two sections of the tape extending at both sides past the open end of the test tube towards a lower end of the test tube. Upon picking up the test tubes, generally, the test tubes can be arranged in a vertical orientation. Hence, the sections of the tape next to the test tube can be forced downwards. In one embodiment, the two sections of the tape extending at both sides past the open end can be pulled downwards substantially in parallel to a longitudinal direction of the test tubes. In one embodiment, the two sections can be pulled diagonally downwards.

The tape length required for covering one test tube can be, for example, about 5 cm to 30 cm. In one embodiment, the tape can be provided in the form of a strip having a short length of about 5 to 30 cm. In some embodiments, a tape having a length, which can be longer than the tape length required for covering one test tube, can be provided where the tape runs between a tape supply unit and a take-up unit. The tape can be section-by-section withdrawn from the tape supply for covering successive test tubes. After releasing the test tube, the used section of the tape can be drawn into the take-up unit. In some embodiments, several meters of tape can be initially stored in the tape supply unit. The tape supply unit and the take-up unit in some embodiments can each comprise a reel from which or to which the tape can be wound. In some embodiments, the take-up unit can be provided with a mechanism avoiding a withdrawal of used tape from the take-up unit. For example, a reel provided at the take-up unit can be mounted unidirectional rotatable for avoiding unwinding of used tape.

In some embodiments, no section of a tape can be reused for covering successive tubes. For this purpose, in some embodiments, the tape can be forwarded from the tape supply unit to the take-up unit prior to covering the open ends of successive test tubes. Hence, a new section of the tape can be used for each test tube avoiding that a potentially contaminated section of the tape coming in contact with the sample. The forwarding may be carried out either immediately prior to the handling of a particular test tube and/or after handling of a test tube in preparation of a handling of a subsequent test tube.

A device for handling an open test tube in a laboratory automation system by a manipulator with a retaining area for the test tube is also provided. The device can comprise a residue-free, removable, flat cover element arranged for being forced against the open end of a test tube retained in the retaining area. In the context of the present disclosure, a manipulator can refer to a robotic mechanism having a tool or work unit attached to its distal end. The manipulator, for example, can be a pick-and-place manipulator having a gripper attached to its distal end. The device, in some embodiments, can be attached to the manipulator, for example the pick-and-place manipulator, in particular to the tool, for example a gripper. Hence, covering the test tube can be carried out upon handling the test tube by the manipulator. The device can be used, for example, with a manipulator sorting open test tubes. A position of a test tube within a rack can be altered and/or a test tube can be moved from a first rack to a second rack and/or for moving test tubes between various stations, supply chains and other devices of the laboratory automation system.

In some embodiments, the cover element can be a tape such as, for example, an aluminum tape, a copper tape and/or a plastic tape, for example, a cling tape. The material of the tape can be chosen suitably by the person skilled, avoiding any potential interaction with the sample and/or any residue that may result in a contamination of the sample. The tape in one example can be provided with a coating which can be unreactive under expected conditions.

According to some embodiments, the device can comprise a support plate attachable to the manipulator for arranging the tape in the retaining area. The support plate can be mounted in one embodiment to a limb or arm of the manipulator. In other embodiments, the device can be mounted to a tool of the manipulator, for example, to a gripper. The support plate can be designed to prevent a collision with the tool of the manipulator. In some embodiments, a fork-shaped support plate can be provided having two tines extending in parallel at two sides of the tool.

In one embodiment, the tape can be held by the support plate at a fixed position in the retaining area. In one embodiment, the device can comprise a support plate for supporting the tape moveable with respect to the Z-axis of the manipulator, in particular, moveable relative to the tool of the manipulator. In the context of the present disclosure, the term Z-axis can refer to the axis parallel to the tool axis, i.e., with a pick-and-place manipulator generally to the vertical axis. A movable support plate can allow an adjustment of the position of the support plate to a height of the test tube. In one embodiment, the support plate can be moveable over a distance to allow the tape to be moved out of the retaining area, for example, when handling a capped tube and/or in case of an unexpected disturbance. For this purpose, in some embodiments, a driving device can be assigned to the support plate for moving the support plate along the Z-axis.

Due to gravitational forces, the support plate can be forced downwards. In some embodiments, the support plate can be forced along the Z-axis towards a tool tip of the manipulator by a force element such as, for example, by at least one compression spring.

The device, in some embodiments, can comprise a tape supply unit and a take-up unit. The tape can run between the tape supply unit and the take-up unit. In some embodiments, the tape supply unit and the take-up unit can both be provided with a reel.

In one embodiment, prior to covering the open end of the test tube, the tape can be forwarded manually from the take supply unit to the take-up unit for removing a potentially contaminated section of the tape. In some embodiments, a driving device can be assigned to the take-up unit for forwarding the tape from the tape supply unit to the take-up unit.

In some embodiments, the driving device can be synchronized with the manipulator such that upon releasing a test tube, the tape can be forwarded for removing a potentially contaminated section of the tape. Hence, upon releasing one test tube, the tape can be prepared for a subsequent test tube.

The manipulator, in some embodiments, can comprise a gripper with at least two fingers extending in the direction of the Z-axis for picking-up and retaining the test tube. The tape can run between the at least two fingers with a flat face of the tape prior to picking-up the test tube oriented substantially perpendicular to the Z-axis. This arrangement can allow for a compact device while avoiding an undesired interference of the gripper and the tape. Upon approaching the test tubes, the open end can come into contact with the tape reaching across the retaining area and, upon further movement of the gripper towards the test tubes, the tape sections adjacent to the open end can be pushed downwards, thereby stretching the tape over the open end.

A laboratory automation system with a number of pre-analytical, analytical and/or post-analytical stations for carrying out the disclosed method and/or with the disclosed device is provided.

Figure 2:
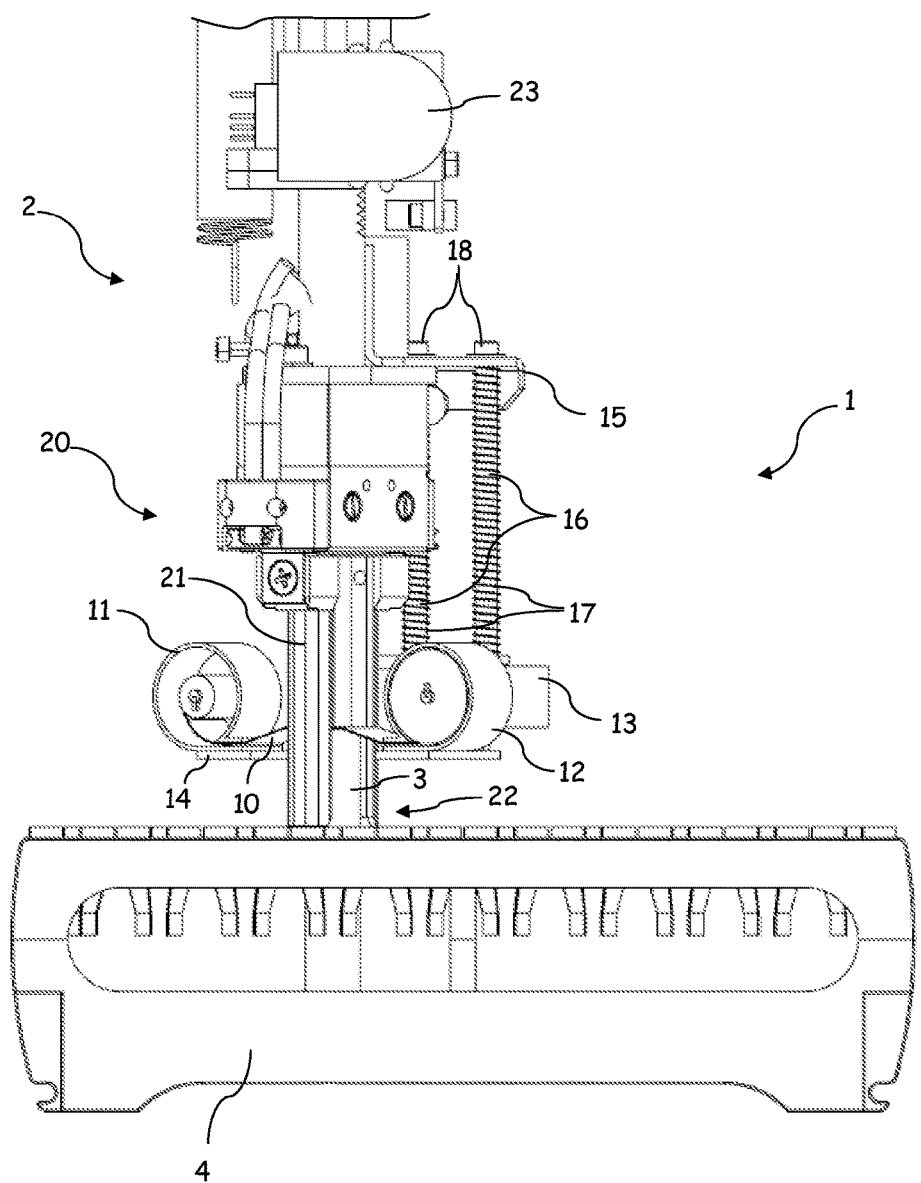
FIG. 2 illustrates a front view of the device of FIG. 1 according to an embodiment of the present disclosure.
Figure 3:
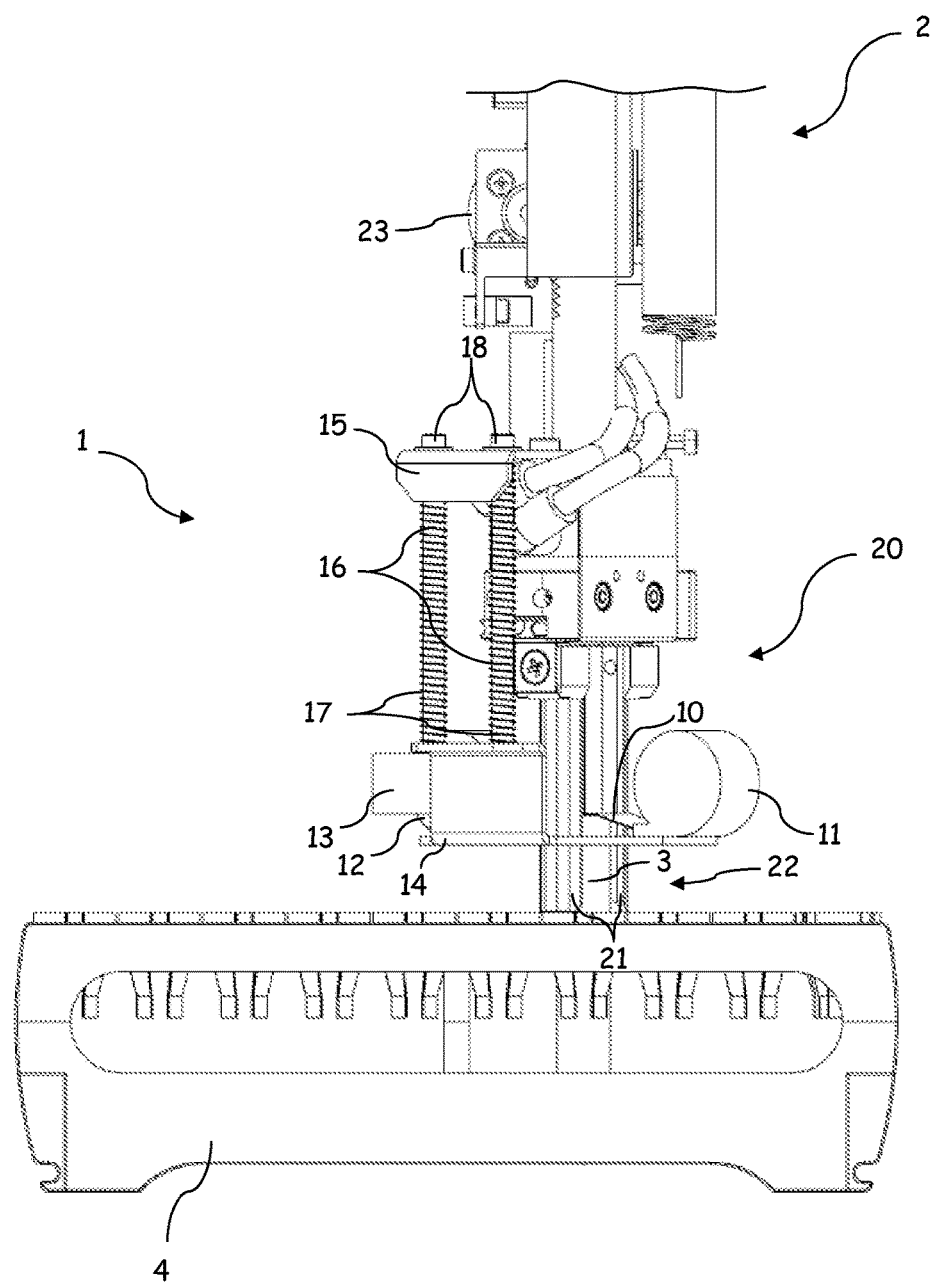
FIG. 3 illustrates a rear view of the device of FIG. 1 according to an embodiment of the present disclosure.

FIGS. 1 to 3 show in schematic drawings an embodiment of a device 1 for handling open test tubes in a perspective view, a front view, and a rear view, respectively. The device 1 can be attached to a manipulator 2 for handling test tubes in a laboratory automation system. At least prior to being picked-up by the manipulator 2, in the embodiment shown, the test tubes 3 can be placed in a rack 4, only one test tube 3 is shown in FIGS. 1-3. The manipulator 2 can remove the tubes 3 from the rack 4, for example, for sorting the test tubes. A position of a test tube 3 within the rack 4 can be altered and/or a test tube 3 can be moved from a first rack to a second rack. Alternatively, the test tube 3 can be taken from the rack 4 and moved to a different station with the laboratory automation system.

The manipulator 2 shown can comprise a gripper 20 with two fingers 21 defining a retaining area 22 for the test tube 3. The gripper 20 can be moveable along a Z-axis indicated with an arrow in FIG. 1 by a driving device 23 for picking-up the test tube 3 from the rack 4 and/or placing the test tube 3 in the rack 4. The fingers 21 can be moveable in a movement direction perpendicular to the Z-axis.

The device 1 can comprise a tape 10, which functions as a residue-free, removable, flat cover element that can be forced against the open end of a test tube 3 retained in the retaining area 22. In one embodiment, the tape 10 can be stretched over the open end of the test tube 3 to sealingly cling to the contour of the open end.

In the embodiment shown, the tape 10 can run between a tape supply unit 11 and a take-up unit 12 between the two fingers 21 with a flat face of the tape 10 oriented substantially perpendicular to the Z-axis, i.e., horizontally in the orientation shown in the figures. For gripping or releasing the test tubes 3, the fingers 21 of the gripper 20 can move perpendicular to the Z-axis. The tape 10 can be arranged crosswise, in particular, perpendicular to the movement direction of the fingers 21. The tape supply unit 11 can comprise a reel from which the tape 10 can be wound. The take-up unit 12 can comprise a reel to which the tape 10 can be wound. A driving device 13 can be assigned to the take-up unit 12. The reel of the take-up unit 12 can be mounted unidirectional rotatable for avoiding unwinding of tape 10 from the reel of the take-up unit 12.

The device 1 can further comprise a support plate 14 to which the tape supply unit 11 and a take-up unit 12 can be mounted. The support plate 14 can be attached to the manipulator 2 by a mounting plate 15, two bolts 16 extending in parallel to the Z-axis, and two compression springs 17 arranged coaxially to the bolts 16. The mounting plate 15 can be arranged at a fixed position of the manipulator 2 with respect to the gripper 20. The mounting plate 15 can be provided with two through holes for the two bolts 16. The bolts 16 can be inserted in the through holes moveable along their longitudinal axis. Stoppers 18 can be provided for limiting the movement of the bolts 16. At the end opposite to the stoppers 18, the bolts 16 can be fixedly coupled to the support plate 14. The compression springs 17 can force the support plate 14 in the direction of the Z-axis away from the mounting plate 15 towards a tip of the gripper 20. The two bolts 16 can allow a reliable guiding of the support plate 14 along the Z-axis. However, in other embodiments, only one bolt, for example, a bolt having not a rotationally symmetric cross section, or more that two bolts 16, can be provided.

In use, the driving device 13 can be activated for driving the reel of the take-up unit 12 so that the tape 10 can be wound to the reel of the take-up unit 12. While driving the reel of the take-up unit 12 for winding the tape 10, the reel of the tape supply unit 11 may not be blocked and tape 10 can be unwound from the reel of the tape supply unit 11. After a new unused section of the tape 10 having a desired length is arranged in the retaining area 22, the reels of the tape supply unit 11 and the take-up unit 12 can both be blocked for preventing an unwinding of the tape 10.

Next, the manipulator 2 can be driven to approach the test tube 3. At this stage, the support plate 14 can be arranged in a position with respect to the gripper 20 which can be closer to a distal end of the gripper 20 than the open end of the test tube 3 will be after the gripper 20 has reached its final position for picking up the test tube 3 and the fingers 21 for gripping the test tube 3 are approaching each other. As a result, the support plate 14 can be arranged below the open end of the test tube 3 arranging the tape 10 in an area at which the test tube 3 can be received. Hence, the open end of the test tube 3 can contact the tape 10 when the manipulator 2 approaches the test tube 3. Due to the contact of the open end of the test tube 3 and the tape 10, a force can be exerted on the tape 10 forcing the tape 10 in the direction of the Z-axis out of the retaining area 22 towards the mounting plate 15. The force can be counteracted by the compression springs 17. In result, two sections of the tape 10 extending at both sides past the open end of the test tube 3 can be forced diagonally towards a lower end of the test tube 3. Thereby, the tape 10 can be stretched and forced under tension against the open end of the test tube 3. Hence, by use of the tape 10, the test tube 3 can be sealingly covered and the tape 10 can prevent a sample in the test tube 3 from sloshing out of the test tube 3 or spilling when moving the test tube by the manipulator 2. The tape 10 clinging to the open end can permit a handling of the covered test tube 3 at high velocities and/or at high accelerations. Hence, in contrast to prior art devices, it may not be necessary to lower the speed of the manipulator 2 even in case of a high fill level.

After or upon releasing the test tube 3 by opening the fingers 21 of the gripper 20 and moving the gripper 20 away from the test tube 3 along the Z-axis, the driving device 13 assigned to the take-up unit 12 can be activated for forwarding the tape 10 from the tape supply unit 11 to the take-up unit 12. Thereby, a potentially contaminated section of the tape 10 can be removed and a clean section of the tape 10 can be provided between the tape supply unit 11 and the take-up unit 12. Thereafter, the manipulator 2 may be driven to pick-up a further test tube, the open end of which can be covered by the clean section of the tape 10.

In some embodiments, an additional driving device can be assigned to the device 1 for moving the support plate 14 with the tape 10 towards the mounting plate 15. This can allow an automated adjustment of the position of the support plate 14 along the Z-axis to a height of a test tube. Further, the additional driving device can allow for an active movement of the support plate 14 out of the retaining area 22 for avoiding collision and/or when picking up a capped test tube.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A device for moving a test tube in a laboratory automation system, the device comprises:

a test tube having an open end;

a manipulator including a gripper with two fingers extending along the longitudinal axis of the manipulator for picking up and retaining the test tube, wherein the space between the two fingers define a retaining area;

a residue-free tape;

a support plate movably attached to the manipulator for supporting the tape and for arranging the tape in the retaining area, the support plate is movable along the longitudinal axis of the manipulator;

a tape supply unit mounted to the support plate;

a tape take-up unit mounted to the support plate, wherein the tape runs between the tape supply unit and the take-up unit in the retaining area and wherein the tape runs between the two fingers with a flat-face of the tape prior to picking up the test tube oriented along the longitudinal axis of the manipulator;

a force element, wherein the force element is attached to the support plate, such that the support plate is forced along the longitudinal axis of the manipulator by the force of the force element;

a controller configured to control the gripper to pick up the test tube such that the support plate is forced downward along the longitudinal axis of the manipulator by the force element to force the tape against the open end of the test tube retained in the retaining area.

2. The device according to claim 1, wherein the tape is an aluminum tape, a copper tape, a plastic tape, a cling tape, or combinations thereof.

3. The device according to claim 1, wherein the force element comprises at least one compression spring.

4. The device according to claim 1, further comprises
a driving device assigned to the take-up unit for forwarding the tape from the tape supply unit to the take-up unit prior to covering the open end of the test tube.

5. The device according to claim 4, wherein the driving device is synchronized with the manipulator such that upon or after releasing a test tube, the tape is forwarded for removing a potentially contaminated section of the tape.

6. The device according to claim 1, wherein the manipulator comprises a gripper for picking up a test tube.

* * * * *